United States Patent [19]

Blank

[11] Patent Number: 5,620,965

[45] Date of Patent: Apr. 15, 1997

[54] SALICYLIC ACID FOR REGULATING SKIN WRINKLES AND/OR SKIN ATROPHY

[75] Inventor: Roy L. Blank, Spring Valley, N.Y.

[73] Assignee: Richardson-Vicks Inc., Shelton, Conn.

[21] Appl. No.: 689,470

[22] Filed: Aug. 7, 1996

Related U.S. Application Data

[60] Continuation of Ser. No. 465,027, Jun. 5, 1995, Pat. No. 5,573,759, which is a division of Ser. No. 434,250, May 3, 1995, abandoned, which is a continuation of Ser. No. 28,756, Mar. 9, 1993, abandoned, which is a continuation of Ser. No. 796,750, Nov. 25, 1991, abandoned.

[51] Int. Cl.$^6$ ............................ A61K 31/60; A61K 7/42; A61K 7/40

[52] U.S. Cl. ............................ 514/159; 424/59; 424/60; 574/844; 574/847

[58] Field of Search ..................................... 514/159, 844, 514/847; 424/59, 60

[56] References Cited

U.S. PATENT DOCUMENTS

| | | | |
|---|---|---|---|
| 3,821,370 | 6/1974 | Tenta | 424/145 |
| 4,542,129 | 9/1985 | Orentreich | 514/178 |
| 4,603,146 | 7/1986 | Kligman | 514/559 |
| 4,608,370 | 8/1986 | Aronsohn | 514/159 |
| 4,877,805 | 10/1989 | Kligman | 514/381 |
| 4,888,342 | 12/1989 | Kligman | 514/419 |
| 4,891,227 | 1/1990 | Thaman et al. | 424/443 |
| 4,891,228 | 1/1990 | Thaman et al. | 424/443 |
| 4,938,960 | 7/1990 | Ismail | 514/556 |
| 5,001,156 | 3/1991 | Philippe et al. | 514/881 |
| 5,017,367 | 5/1991 | Stojkoski | 424/63 |

FOREIGN PATENT DOCUMENTS

| | | |
|---|---|---|
| 88-191753/28 | 7/1988 | European Pat. Off. . |
| 89-403474 | 12/1989 | European Pat. Off. . |
| 90-225614/30 | 7/1990 | European Pat. Off. . |
| 51-073-137 | 6/1976 | Japan . |
| 2179858 | 3/1987 | United Kingdom . |

OTHER PUBLICATIONS

Harry, Ralph G., The Principles and Practice of Modern Cosmetics, 1963, vol. Two, pp. 401 and 402.

Harry, Ralph G., The Principles and Practice of Modern Cosmetics, 1950, vol. Two, pp. 163, 164, 272, and 273.

Document Number CA97(18):150742k Date Aug. 12, 1982 Country Germany.

Document Number CA86(24):177334p Date Mar. 17, 1977 Country Germany.

Document Number CA88(20):141686g Date Jun. 29, 1977 Country South Africa.

Document Number CA102(4):32260a Date Jul. 1, 1984 Country Czechoslovakia.

Document Number CA109(24)216030b Date Apr. 13, 1988 Country Japan.

Document Number CA91(6):44523f Date Mar. 10, 1979 Country Japan.

*Primary Examiner*—Shelley A. Dodson
*Attorney, Agent, or Firm*—David K. Dabbiere; Anthony D. Sabatelli

[57] ABSTRACT

The present invention relates to a method for regulating wrinkles and/or atrophy in mammalian skin comprising treating the skin with a safe and effective amount of salicylic acid and/or additional active component.

2 Claims, No Drawings

SALICYLIC ACID FOR REGULATING SKIN WRINKLES AND/OR SKIN ATROPHY

This is a continuation of application Ser. No. 08/465,027, filed on Jun. 5, 1995, now U.S. Pat. No. 5,573,759, which is a divisional of application Ser. No. 08/434,250, filed on May 3, 1995, abandoned, which is a continuation of application Ser. No. 08/028,756, filed on Mar. 9, 1993, abandoned, which is a continuation of application Ser. No. 07/796,750, filed on Nov. 25, 1991, abandoned.

TECHNICAL FIELD

The present invention relates to the field of the anti-aging of skin. Specifically, the invention relates to novel methods for effacing and preventing wrinkles in mammalian skin.

BACKGROUND OF THE INVENTION

Skin is subject to abuse by many extrinsic (environmental) factors as well as intrinsic (chronoaging) factors. A common extrinsic factor is exposure to ultraviolet radiation. Whether extrinsic or intrinsic, the abuse results in wrinkling of the skin. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

Chronoaging results in the thinning and general degradation of skin. As the skin naturally ages, there is a reduction in the cells and blood vessels that supply the skin. There is also a flattening of the dermal-epidermal junction which results in weaker mechanical resistance of this junction. As a consequence, older persons are more susceptive to blister formation in cases of mechanical trauma or disease processes. (See Oikarinen, (1990) "The Aging of Skin: Chronoaging Versus Photoaging", *Photodermatol. Photoimmunol. Photomed.*, Vol. 7, pp 3–4).

It is known to use salicyclic acid for the treatment of acne, see for example, U.S. Pat. Nos. 4,891,227 and 4,891,228, to Thaman et al., both issued Jan. 2, 1990 the disclosure of which are incorporated herein. Further, salacyclic acid has been used for the removal of wart, corns and calluses; for the treatment of psoriasis, seborrheic dermatitis and dandruff; and for the topical treatment of ringworm infection. A listing of commercially available products containing salicyclic acid will be found in the Physician's Desk Reference, 45th Edition, 1991, page 323. However, these prior art uses of saliciylic acid have generally involved short term treatments in which relatively large doses of the acid are applied (i.e., sufficient to cause significant irritation and often peeling) in order to obtain a cure or treatment of the particular condition, such as removal of comedones, as opposed to persistent treatment of normal aging skin.

OBJECTS OF THE PRESENT INVENTION

It is an object of the present invention to provide a method of regulating wrinkles and/or atrophy in mammalian skin which comprises treating mammalian skin with a safe and effective amount of an anti-wrinkle/anti-atrophy agent.

SUMMARY OF THE INVENTION

The present invention relates to a method for regulating wrinkles and/or atrophy in mammalian skin comprising chronic treatment of the skin with a safe and effective amount of salicylic acid.

All percentages and ratios used herein are by weight and all measurements are at 25° C. unless otherwise indicated.

DETAILED DESCRIPTION OF THE INVENTION

As used herein, "alkyl" means an unsubstituted carbon-containing chain which may be straight, branched or cyclic, preferably straight or branched, more preferably straight; saturated, monounsaturated (i.e., one double or triple bond in the chain), or polyunsaturated (i.e., two or more double bonds in the chain; two or more triple bonds in the chain; one or more double and one or more triple bonds in the chain), preferably saturated.

As used herein, "topical application" means directly laying on or spreading on outer skin.

As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "regulating wrinkles" means preventing, retarding, arresting, or reversing the process of wrinkle formation in mammalian skin.

As used herein, "skin atrophy" means the thinning and/or general degradation of the dermis often characterized by a decrease in collagen and/or elastin as well as decreased number, size and doubling potential of fibroblast cells. Skin atrophy is a natural result of aging. Skin atrophy is often an undesirable side effect resulting from treatment with coricosteroids.

As used herein, "regulating skin atrophy" means preventing, retarding, arresting, or reversing the process of atrophy in mammalian skin.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "chronic treatment" means continued treatment with an active agent over an extended period during a subject's lifetime, preferably for at least about three weeks, more preferably from about three months to about twenty years, more preferably from about six months to about ten years, more preferably still from about one year to about five years.

As used herein, all percentages are by weight unless otherwise specified.

Active Compound

The present invention relates a method for regulating wrinkles and/or atrophy in mammalian skin comprising treating the skin with a safe and effective amount of a composition comprising an salicyclic acid active component. The salicylic acid active component can be salicylic acid alone, salicylic acid derivatives and salicylic acid in combination with other active ingredients described below. Most preferred is salicylic acid in a hydroalcoholic solution.

Salicyclic acid is a well known active component and is generally described in U.S. Pat. No. 4,514,385, to Damani, et al., assigned to Alcon Laboratories, issued Apr. 30, 1985.

The preferred topical carrier comprises a hydroalcoholic solution at pH 2 to 4 of salicylic acid as the active anti-acne ingredient together with a specific anionic surface component. More preferably such active is a stable, hydroalcoholic composition having a pH value of from 2 to 4 and containing from about 0.2 to about 5.0 percent by weight of salicylic acid and from about 0.2 to about 5.0 percent by weight of sodium methyl cocoyl taurate and/or sodium methyl oleoyl taurate as the anionic surfactant component. Generally, a sufficient amount of a cosmetically acceptable alkaline component (i.e., alkalizing agent) to provide and maintain the composition with a pH from about 2.0 to about 4 is included.

As the alcohol component of the hydroalcoholic solvent, from about 10 to about 60 percent by weight of ethyl alcohol, measured as total $C_2H_5OH$ content, is preferred although a like amount of isopropyl alcohol ($C_3H_7OH$) may also be beneficially utilized. From about 30 to about 80 percent by weight of water is also required as the aqueous component of the hydroalcoholic solvent.

The anionic surfactant component of this active composition, i.e., the taurate surfactant component, is specifically directed to sodium methyl cocoyl taurate and sodium methyl oleoyl taurate, both of which are readily available from diverse commercial suppliers, as noted in The Cosmetic, Toiletry and Fragrance Association (CTFA) Cosmetic Ingredient Dictionary, 3rd Edition, 1982, pages 286–287.

Although it is preferred to use the taurate surfactant as the sole surfactant in the active compositions, other surfactants may be included, the nonionic type having preference over the anionic type in view of the relative non-irritating characteristic to the skin of the former. Cationic type surfactants, which are most irritating to the skin, are less preferred because of their marked susceptibility to hydrolysis at the low acidic pH of the subject compositions.

The pH value of the preferred active component, from about 2 to about 3.5, may be achieved by use of appropriate cosmetically acceptable primary or dual buffer systems. In most instance, the resultant pH of the hydroalcoholic solution of salicylic acid is slightly below or at the lower end of the indicated range, and all that is required to adjust the pH to a desired higher value within the indicated range is to add an alkaline additive such as is commonly utilized in cosmetic formulations for such purpose. Although sodium carbonate is preferred, other suitable alkalizing agents include potassium carbonate, sodium hydroxide, potassium hydroxide, triethanolamine and the like. If deemed necessary to change or adjust the pH to a lower value, a suitable cosmetically acceptable acidifying agent such as citric acid may be employed.

Pharmaceutical Compositions

In a preferred embodiment, treatment will employ the use of a topical pharmaceutical composition comprising the active compound and a pharmaceutically-acceptable carrier. The term "pharmaceutically-acceptable carrier", as used herein, means one or more compatible solid or liquid filler diluents or microencapsulating substances which are suitable for administration to a human or lower animal. Pharmaceutically-acceptable carriers must be of sufficiently high purity and sufficiently low toxicity to render them suitable for administration to the human or lower animal being treated. A safe and effective amount of carrier is from about 50% to about 99.99%, preferably from about 99.9% to about 80%, more preferably from about 98% to about 95%, of the composition.

Variations in formulation of these carriers will result in a wide variety of products which fall within the scope of the present invention.

The topical pharmaceutical compositions of the present invention may be made into a wide variety of product types. These include, but are not limited to solutions, lotions, creams, beach products, gels, sticks, sprays, pads, ointments, pastes, mousses and cosmetics. These product types may comprise several types of carrier systems including, but not limited to solutions, emulsions, gels and solids.

The topical pharmaceutical compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the active compound, and possesses acceptable safety properties (e.g., irritation and sensitization characteristics). Water is a typical aqueous solvent. Examples of suitable organic solvents include: propylene glycol, butylene glycol, polyethylene glycol (200–600), polypropylene glycol (425–2025), glycerol, 1,2,4-butanetriol, sorbitol esters, 1,2,6-hexanetriol, ethanol, isopropanol, butanediol, and mixtures thereof. Preferably, these solutions contain from about 0.01% to about 50% of the active compound, more preferably from about 0.1% to about 20%; and from about 1% to about 80% of an acceptable aqueous or organic solvent, more preferably from about 1% to about 40%.

If the topical pharmaceutical compositions of the present invention are formulated as an aerosol and applied to the skin as a spray-on, a propellant is added to a solution composition. A more complete disclosure of propellants useful herein can be found in Sagarin, *Cosmetics Science and Technology*, 2nd Edition, Vol. 2, pp. 443–465 (1972).

Topical pharmaceutical compositions of the present invention may be formulated as a solution comprising an emmolient. An example of a composition formulated in this way would be a sunscreen-containing product. Preferably, such compositions contain from about 0.1% to about 50% of the active compound and from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions preferably comprise from about 0.1% to about 20%, more preferably from about 1% to about 5%, of the active compound; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the present invention would preferably comprise from about 0.1% to about 20%, more preferably from about 1% to about 5%, of the active compound; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72–73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. Nos. 3,755,560, issued Aug. 28, 1973, Dickert et al; 4,421,769, issued Dec. 20, 1983, Dixon et al.; and McCutcheon's *Detergents and Emulsifiers*, North American Edition, pages 317–324 %(1986); the disclosures of which are incorporated herein by reference. Preferred emulsifiers are anionic or nonionic, although the other types may also be used.

Lotions and creams can be formulated as emulsions as well as solutions. Preferably such lotions comprise from about 0.1% to about 20%, more preferably from about 1% to about 5%, of the active compound; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would preferably comprise from about 0.1% to about 20%, more preferably from about 1% to about 5%, of the active compound; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the present invention. Multiphases emulsion compositions, such as the water-in-oil-in-water type, as disclosed in U.S. Pat. No. 4,254,105, Fakuda et al., issued Mar. 3, 1981, incorporated herein by reference, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. Pat. No. 4,960,764, Figueroa, issued Oct. 2, 1990, are also useful in the present invention. Preferably, this triple emulsion carrier system can be combined with from about 0.1% to about 20%, more preferably from about 1% to about 5%, of the active compound to yield the topical pharmaceutical composition of the present invention.

Another emulsion carrier system useful in the topical pharmaceutical compositions of the present invention is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is preferably combined with from about 1% to about 5% of the active compound.

If the topical pharmaceutical compositions of the present invention are formulated as a gel or a cosmetic stick, a suitable amount of a thickening agent, as disclosed supra, is added to a cream or lotion formulation.

The topical pharmaceutical compositions of the present invention may also be formulated as makeup products such as foundations.

The topical pharmaceutical compositions of the present invention may also be formulated as medicated pads. Suitable examples of these pads are fully disclosed in U.S. Pat. Nos. 4,891,227 and 4,891,228, to Thaman et al., both issued Jan. 2, 1990 the disclosures of which are incorporated herein.

The topical pharmaceutical compositions of the present invention may contain, in addition to the aforementioned components, a wide variety of additional oil-soluble materials and/or water-soluble materials conventionally used in topical compositions, at their art-established levels.

Various water-soluble materials may also be present in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical pharmaceutical compositions of the present invention may also include a safe and effective amount of a penetration enhancing agent. A preferred amount of penetration enhancing agent is from about 1% to about 5% of the composition. Another useful penetration enhancer for the present invention is the non-ionic polymer under the CTFA designation: polyacrylamide and isoparaffin and laureth-7, available as Sepigel from Seppic Corporation. Also useful is polyquaternium-32 and mineral oil known as SalCare SC92 available from Allied Colloids, Suffolk, Va. This is a class of cationic polymers which are generally described in U.S. Pat. Nos. 4,628,078 to Glover et al. issued Dec. 9, 1986 and 4,599,379 to Flesher et al. issued Jul. 8, 1986 both of which are incorporated by reference herein.

Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European Patent Application 0043738, Cooper et al., published Jan. 13, 1982.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Vitamins

Various vitamins may also be included in the compositions of the present invention. For example, Vitamin A, ascorbic acid, Vitamin B, biotin, panthothenic acid, Vitamin D, Vitamin E and mixtures thereof and derivatives thereof may be used.

Cleaning Compositions

The skin cleaning compositions of the present invention comprise, in addition to the active compound, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the active compound in a manner such that there is no interaction which would substantially reduce the efficacy of the composition for regulating skin wrinkles and/or skin atrophy.

The skin cleaning compositions of the present invention preferably contain from about 0.1% to about 20%, preferably from about 1% to about 5%, of the active compound and from about 1% to about 90%, more preferably from about 1% to about 10%, of a cosmetically-acceptable surfactant.

The physical form of the skin cleansing compositions is not critical. The compositions can be, for example, formulated as toilet bars, liquids, pastes, mousses, or pads.

The surfactant component of the compositions of the present invention are selected from anionic, nonionic, zwitterionic, amphoteric and ampholytic surfactants, as well as mixtures of these surfactants. Such surfactants are well-known to those skilled in the detergency art.

The cleaning compositions of the present invention can optionally contain, at their art-established levels, materials which are conventionally used in skin cleansing compositions.

Combination Actives
A. Sunscreens and Sunblocks

Optimum regulation of skin wrinkling resulting from exposure to U.V. light can be obtained by using a combination of the salicylic acid active of the present invention together with sunscreens or sunblocks. Useful sunblocks include, for example, zinc oxide and titanium dioxide.

Photodamage is a predominant cause of skin wrinkling. Thus, for purposes of wrinkle prevention, the combination of the active compound with a UVA and/or UVB sunscreen would be most desirable. The inclusion of sunscreens in compositions of the present invention will provide immediate protection against acute UV damage. Thus, the sunscreen will prevent further wrinkle formation caused by UV radiation, while the active compound regulates existing wrinkles and skin atrophy.

A wide variety of conventional sunscreening agents are suitable for use in combination with the active compound. Segarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyercyl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (methyl and benzyl esters, α-phenyl cinnamonitrile; butyl cinnamoyl pyruvate); Dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinone salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acid; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-di-benzoylmethane.

Preferred sunscreens useful in the compositions of the present invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

A safe and effective amount of sunscreen may be used in the compositions of the present invention. The sunscreening agent must be compatible with the active compound. Generally the composition may comprise from about 1% to about 20%, preferably from about 2% to about 10%, of a sunscreening agent. Exact amounts will vary depending upon the sunscreen chosen and the desired Sun Protection Factor (SPF).

Also particularly useful in the present invention are sunscreens such as those disclosed in Sabatelli, U.S. patent application Ser. No. 054,085 (filed Jun. 2, 1987) and Sabatelli et al., U.S. patent application Ser. No. 054,046 (filed Jun. 2, 1987). The sunscreening agents disclosed therein have, in a single molecule, two distinct chromphore moieties which exhibit different ultra-violet radiation absorption spectra. One of the chromophore moieties absorbs predominantly in the UVB radiation range and the other absorbs strongly in the UVA radiation range.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred wrinkle and atrophy regulating composition of the present invention, an anti-inflammatory agent is included as an active agent along with the active compound. The inclusion of an anti-inflammatory agent enhances the wrinkle regulating benefits of the compositions. The anti-inflammatory agent protects strongly in the UVA radiation range (though it also provides some UVB protection as well) thereby preventing further wrinkle formation caused by UV radiation, while the active compound regulates existing wrinkles and skin atrophy. Thus the combination provides broad protection. The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide. betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects, etc., of nonsteroidal anti-inflammatory agents, reference may be had to standard texts, including *Antiinflammatory and Anti-Rheumatic Drugs,* K. D. Rainsford, Vol. I–III, CRC Press, Boca Raton, (1985), and *Anti-inflammatory Agents, Chemistry and Pharmacology,* 1, R. A. Scherrer et al., Academic Press, New York (1974).

Specific non-steroidal anti-inflammatory agents useful in the composition of the present invention include, but are not limited to:

1) the oxicams, such as piroxicam, isoxicam, tenoxicam, sudoxicam, and CP-14,304;

2) the salicylates, such as aspirin, disalcid, benorylate, trilisate, safapyrn, solprin, diflunisal, and fendosal;

3) the acetic acid derivatives, such as dichlofenac, fenclofenac, indomethacin, sulindac, tolmetin, isoxepac, furofenac, tiopinac, zidometacin, acetamacin, fentiazac, zomepiract, clidanac, oxepinac, and felbinac;

4) the fenamates, such as mefenamic, meclofenamic, flufenamic niflumic, and tolfenamic acids;

5) the propionic acid derivatives, such as ibuprofen, naproxen, benoxaprofen, flurbiproflen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefanamic acid, meclofenamic acid, piroxicam and felbinac are preferred; ibuprofen, naproxen, and flufenamic acid are most preferred.

Another class of anti-inflammatory agents which are useful in the present invention are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-t-butylphenol; 4-((S)-(−)-3'-methyl-5'-hexynoyl)-2,6-di-t-butylphenol; 4-((R)-(+)-3'-methyl-5'-hexynoyl)-2,6-di-t-butylphenol; and 4-(3',3'-dimethoxypropionyl)-2,6-di-t-butylphenol are useful in the present invention.

Yet another class of anti-inflammatory agents which are useful in the present invention are those disclosed in U.S. Pat. No. 4,912,248, Mueller, Issued Mar. 27, 1990. This patent discloses compounds and diastereomeric mixtures of specific 2-naphthyl-containing ester compounds, especially naproxen ester and naproxol ester compounds, having two or more chiral centers.

Finally, so-called "natural" anti-inflammatory agents are useful in the present invention. For example, candelilla wax, alpha bisabolol, aloe vera, Manjistha (extracted from plants in the genus Rubia, particular *Rubia cordifolia*), and Guggal (extracted from plants in the genus Commiphora, particularly *Commiphora mukul*), may be used.

C. Anti-Oxidants/Radical Scavengers

In a preferred wrinkle and atrophy regulating composition of the present invention, an anti-oxidant/radical scavenger is included as an active agent along with the active compound. The inclusion of an anti-oxidant/radical scavenger increases the wrinkle regulating benefits of the composition.

A safe and effective amount of an anti-oxidant/radical scavenger may be added to the compositions of the present invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

D. Chelators

In a preferred wrinkle and atrophy regulating composition of the present invention, a chelating agent is included as an active agent along with the active compound. As used herein, "chelating agent" means an active agent capable of removing a metal ion from a system by forming a complex so that the metal ion cannot readily participate in or catalyze chemical reactions. The inclusion of a chelating agent increases the wrinkle regulating benefits of the composition.

A safe and effective amount of a chelating agent may be added to the compositions of the present invention, preferably from about 0.1% to about 10%, more preferably from about 1% to about 5%, of the composition. Chelators useful in compositions of the present invention are disclosed in U.S. patent application Ser. No. 251,910, Bissett, Bush & Chatterjee, filed Oct. 4, 1988, incorporated herein by reference. Preferred chelators useful in compositions of the present invention are furildioxime and derivatives thereof, more preferably amphi-2-furidioxime.

E. Retinoids

In a preferred wrinkle and atrophy regulating composition of the present invention, a retinoid, preferably retinoic acid, is included as an active agent along with the active compound. The inclusion of a retinoid increases the wrinkle regulating benefits of the composition. A safe and effective amount of a retinoid may be added to the compositions of the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

F. Benzofuran Derivatives

In a preferred wrinkle and atrophy regulating composition of the present invention, a benzofuran derivative, preferably amiodarone, is included as an active agent along with the active compound. The inclusion of a benzofuran derivative increases the wrinkle regulating benefits of the composition.

A safe and effective amount of a benzofuran derivative may be added to the compositions of the present invention, preferably from about 0.01 to about 20%, more preferably from about 0.1% to about 10%, of the composition. Benzofuran derivatives useful in the present invention are disclosed in U.S. patent application Ser. No. 674,628, Chatterjee and Kapoor, filed Mar. 25, 1991, incorporated herein by reference.

G. N-acetyl-L-cysteine Derivatives

Also preferred for use herein are compounds having the structure

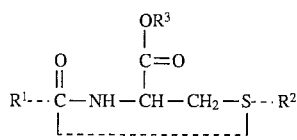

or a pharmaceutically-acceptable salt thereof.

$R^1$ is selected from the group consisting of nil and a $C_1$–$C_{18}$ alkyl, preferably $C_1$–$C_7$, more preferably $C_1$–$C_3$, more preferably still $C_1$ alkyl.

$R^2$ is selected from the group consisting of nil, —H, $C_1$–$C_{18}$ alkyl and

— $R^4$; preferably —H and $C_1$–$C_{18}$ alkyl, more preferably —H. In one embodiment, $R^2$ is preferably a $C_1$–$C_{18}$ alkyl, more preferably $C_1$–$C_7$, more preferably $C_1$–$C_3$, more preferably still $C_1$.

$R^3$ is selected from the group consisting of —H, and $C_1$–$C_{18}$ alkyl, preferably —H. In one embodiment, $R^3$ is preferably a $C_1$–$C_{18}$ alkyl, more preferably $C_1$–$C_7$, more preferably $C_1$–$C_3$, more preferably still $C_1$.

$R^4$ is $C_1$–$C_{18}$ alkyl; preferably $C_1$–$C_7$; more preferably $C_1$–$C_3$; more preferably still $C_1$.

In another embodiment, both $R^1$ and $R^2$ are nil and the carbonyl carbon and the sulfur adjacent $R^1$ and $R^2$, respectively, are covalently bonded to form a cyclic ring. Otherwise, both $R^1$ and $R^2$ are other than nil.

Preferred pharmaceutically-acceptable salts of the active compound include, but are not limited to, sodium, potassium, magnesium, calcium, lithium, rubidium, strontium, aluminum, boron, silicon and zinc salts of the active compound.

Compositions of the present invention comprise from about 0.01% to about 50% of the active compound, preferably from about 0.1% to about 20%, more preferably from about 2% to about 5%.

Zinc complexes which may be formed by zinc and the active compound are useful in the compositions and methods of the present invention.

H. Skin Protectants

In a preferred wrinkle and atrophy regulating composition of the present invention, a safe and effective amount of a skin protectant may be added to the compositions of the present invention, the skin Protestant preferably comprises from about 0.001% to about 2%, more preferably from about 0.01% to about 1% of the composition. Useful skin protectants are disclosed in the *Federal Register* Vol. 48, No. 32 and include allantoin, aluminum hydroxide gel, bismuth subnitrate, boric acid, calamine, cocoa butter, corn starch, dimethicone, glycerin, kaolin, live yeast cell derivative, petrolatum, shark liver oil, sodium bicarbonate, sulfur, tannic acid, white petrolatum, zinc acetate, zinc carbonate and zinc oxide and mixtures thereof.

Other useful components include hormones such as pregnenolone and estrogens. Also useful are the alpha-, or beta-hydroxy acids or alpha-keto acids or derivatives thereof as disclosed in U.S. Pat. No. 4,234,599 to Van Scott et al., issued Nov. 18, 1980 which is incorporated by reference herein. Useful members of this class include alpha-hydroxybutyric acid, alpha-hydroxyisobutyric acid, alpha-hydroxyisocaproic acid, alpha-hydroxyisovaleric acid, atrolactic acid, beta-hydroxybutyric acid, beta-phenyl lactic acid, beta-phenylpyruvic acid, citric acid ethyl pyruvate, glacturonic acid, glucoheptonic acid, glucoheptono 1,4-lactone, gluconic acid, gluconolactone glucuronic acid, glucuronolactone, glycolic acid, isopropyl pyruvate, lactic acid, malic acid, amndelic acid, emthyl pyruvate, mucic acid, pyruvic acid, saccharic acid, saccharic acid 1,4-lactone, tartaric acid and tartronic acid.

Methods for Regulating Wrinkles and/or Skin Atrophy in Mammalian Skin

The present invention relates to a method for regulating wrinkles and/or atrophy in mammalian skin. Such a method comprises treating the skin with a safe and effective amount of the active compound. The amount of active compound and frequency of treatment will vary widely depending upon the level of wrinkling and/or skin atrophy already in existence in the subject, the rate of further wrinkle formation and/or atrophy, and the level of regulation desired.

A preferred method of treating the skin is via chronic topical application of a safe and effective amount of the active compound to regulate wrinkles and/or atrophy in mammalian skin. The amount of active compound and frequency of topical application to the skin can vary widely, depending upon personal needs, but it is suggested as an example that topical application range from about once per week to about 10 times daily, preferably from about twice per week to about 4 times daily, more preferably from about 3 times a week to about 3 times daily, most preferably about once or twice per day. The composition for topical application will comprise from about 0.01% to about 50%, preferably from about 0.1% to about 20%, more preferably from about 1% to about 5% of the active compound. By "chronic" application, it is meant herein that the period of topical application may be over the lifetime of the subject, preferably for a period of at least about three weeks, more preferably from about three months to about twenty years, more preferably from about six months to about ten years, more preferably still from about one year to about five years, thereby resulting in regulation of wrinkles and/or atrophy in mammalian skin.

A preferred method of the present invention for regulating wrinkles and/or atrophy in mammalian skin involves applying both a safe and effective amount of the active compound and a safe and effective amount of one or more of a sunscreening agent, anti-inflammatory agent, Vitamin, antioxidant/radical scavenging agent, chelating agent, retinoid, N-cetyl-L-cysteine derivative, skin protectant and/or benzofuran derivative to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.02 mg to about 1.0 mg per $cm^2$ skin. The amount of anti-inflammatory agent applied is generally from about 0.005 mg to about 0.5 mg, preferably from about 0.01 mg to about 0.1 mg per $cm^2$ skin. The amount of anti-oxidant/radical scavenging agent generally applied is from about 0.001 mg to about 1.0 mg, preferably from about 0.05 mg to about 0.5 mg per $cm^2$ skin. The amount of chelating agent generally applied is from about 0.001 mg to about 1.0 mg, preferably from about 0.01 to about 0.5 mg, more preferably from about 0.05 mg to about 0.1 mg per $cm^2$ skin. The amount of retinoid applied is generally from about 0.00001 mg to about 0.02 mg per $cm^2$ skin, preferably from about 0.001 mg to about 0.01 mg per $cm^2$ skin. The amount of benzofuran derivative applied is generally from about 0.001 mg to about 1.0 mg/$cm^2$ skin per application, preferably from about 0.01 to about 0.5 mg/$cm^2$ skin per application. The amount of active compound applied is generally from about 0.001 mg to about 1.0 mg per $cm^2$ skin per application, preferably from about 0.01 mg to about 0.5 mg per $cm^2$, more preferably from about 0.05 to about 0.25 mg/$cm^2$ skin per application.

In a preferred wrinkle regulating composition of the present invention, compositions comprise one, a combination or all of a sunscreening agent, anti-inflammatory agent, Vitamin, anti-oxidant/radical scavenging agent, chelating agent, retinoid, N-acetyl-L-cysteine derivative, skin protectant and/or benzofuran derivative included as actives along with the active compound. The inclusion of any, a combination or all of these agents with the active compound increases the wrinkle regulating benefits of the composition.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE I

A pad of the present invention is made as follows:

| | Weight % |
|---|---|
| Pad Composition | |
| Substrate A | |
| Cellulose-based nonwoven[1] | 100.0 |
| Substrate B | |
| Polyester (denier = 6)[2] | 45.0 |
| Orlon (denier = 8)[3] | 15.0 |
| Styrene-butadiene resin[4] | 40.0 |
| Laminate | |
| Polyethylene Powder Melt[5] | 100.0 |
| Active Composition | |
| Salicylic acid | 2.0 |
| Na Methyl cocoyl taurate | 3.0 |
| $C_2H_5OH$ (95% ethanol) | 35.0 |
| Witch Hazel distillate | 5.0 |
| Quaternium-22 | 1.0 |
| Menthol | 0.1 |
| Aloe Vera Gel | 0.5 |
| Fragrance | 0.05 |
| Water | q.s. |

[1] Obtained from James River as Airtex Spec 382.
[2] Obtained from Eastern Chemical Company.
[3] Obtained from American Cyanamid.
[4] Obtained from Reichold as tylac 68-500 (ratio of styrene to butadiene 80:20).
[5] Obtained from Quantum Chemical as microthene powder.

Substrate A has a basis weight of about 55 grams per square yard and a loft of about 35 mills. Substrate B has a basis weight of about 65 grams per square yard and a loft of about 70 to 80 mills. The two materials are laminated together by applying a thin coat of Polyethylene power to Substrate A and heating with IR lamps. Substrate A and B are then joined at a hip roll to compress and bond the materials. The resulting nonwoven fabric has a loft of about 90 to 100 mills. The resulting material is then cut into an oval shape (5 cm.×7 cm.). The active components are combined to form a solution and the pad composition is saturated in this solution.

This composition is useful for topical application to regulate skin wrinkles and/or skin atrophy. Use of an amount of the composition to deposit about 2 mg/$cm^2$ of the active compound to the skin is appropriate.

EXAMPLE II

A pad of the present invention is made by combining the following components as in Example I:

| | Weight % |
|---|---|
| Pad Composition | |
| Substrate A | |
| Cellulose-based nonwoven | 100.0 |
| Substrate B | |
| Polyester (denier = 6) | 45.0 |
| Orlon (denier = 8) | 15.0 |
| Styrene-butadiene resin | 40.0 |
| Laminate | |
| Polyethylene Powder Melt | 100.0 |
| Active Composition | |
| Salicylic acid | 2.0 |
| $C_2H_5OH$ (95% ethanol) | 35.0 |
| Glycerin | 2.0 |
| Aloe Vera Gel | 1.0 |
| Menthol | 0.05 |
| Triethanol Amine | 0.7 |
| Fragrance | 0.15 |
| Water | q.s. |

This composition is useful for topical application to regulate skin wrinkles and/or skin atrophy. Use of an amount of the composition to deposit about 2 mg/$cm^2$ of the active compound to the skin is appropriate.

EXAMPLE III

A topical composition is prepared by combining the following components utilizing conventional mixing techniques.

| Active Composition | Weight % |
| --- | --- |
| Salicylic acid | 1.25 |
| Ascorbic acid | 5.00 |
| Na Methyl cocoyl taurate | 1.5 |
| $C_2H_5OH$ (95% ethanol) | 45.0 |
| Witch Hazel distillate | 5.0 |
| Quaternium-22 | 1.0 |
| Menthol | 0.05 |
| Fragrance | 0.05 |
| Water | 41.15 |

This composition is useful for topical application to regulate skin wrinkles and/or skin atrophy. Use of an amount of the composition to deposit about 2 mg/cm$^2$ of the active compound to the skin is appropriate.

EXAMPLE IV

A topical composition is made by combining the following components using conventional mixing technology.

| Ingredient | W/W % |
| --- | --- |
| Water, Purified | 54.0 |
| Alcohol SD 40 | 40.0 |
| Polyacrylamide and $C_{13-14}$ Isoparaffin and Laureth-7[1] | 4.0 |
| Salicylic Acid | 2.0 |

[1] Available as Sepigel from Seppic Corporation.

Water is added to a suitable size container. While mixing at a moderate speed (300 rpm), the polyacrylamide isoparaffin and laureth-7 is added to the water. Separately, the alcohol is placed in a container and covered. Using a Lightnin' Mixer with a 3 blade paddle prop, the salicylic acid is added to the alcohol and mixed at a low speed (100 rpm) until all salicylic acid is dissolved. The alcohol is slowly added to the water phase to form a gel. The resulting gel is mixed at moderate speed until uniform.

This composition is useful for topical application to regulate skin wrinkles and/or skin atrophy. Use of an amount of the composition to deposit about 2 mg/cm$^2$ of the active compound to the skin is appropriate.

EXAMPLE V

A topical composition is made by combining the following components using conventional mixing technology as in Example IV.

| Ingredient | W/W % |
| --- | --- |
| Water | q.s. |
| Alcohol SD 40 | 40.0 |
| Salcare SC92[1] | 3.0 |
| Salicylic Acid | 2.0 |
| Menthol | 0.05 |
| $N_{a_2}EDTA$ | 0.05 |
| Glycerin | 2.00 |

[1] Salcare SC92 is a copolymer of acylamide and a cationic acrylate available from Allied Colloids.

This composition is useful for topical application to regulate skin wrinkles and/or skin atrophy. Use of an amount of the composition to deposit about 2 mg/cm$^2$ of the active compound to the skin is appropriate.

What is claimed is:

1. A method for preventing, retarding, arresting, or reversing wrinkles or atrophy in mammalian skin comprising treating the skin with a safe and effective amount of a composition comprising:
(a) a safe and effective amount of salicylic acid,
(b) a safe and effective amount of a penetration enhancing agent, and
(c) a pharmaceutically-acceptable carrier.

2. A method according to claim 1 wherein said penetration enhancing agent is selected from the group consisting of polyacrylamide, polyquaternium 32, and mixtures thereof.

* * * * *

UNITED STATES PATENT AND TRADEMARK OFFICE
CERTIFICATE OF CORRECTION

PATENT NO.     :     5,620,965              Page 1 of 2
DATED          :     April 15, 1997
INVENTOR(S)    :     Roy Lonnie Blank It is certified that error appears in the above-identified patent and that said Letters Patent is hereby corrected as shown below:

On the title page, item [54]:

In the title, before "SALICYLIC" insert --USE OF--.

At column 1, line 1 before "SALICYLIC" insert --USE OF--.

At column 1, line 14 "of the anti-aging" should read --of anti-aging--.

At column 1, line 41 "disclosure" should read --disclosures--.

At column 1, line 46 "salicyclic" should read --salicylic--.

At column 2, line 33 "coricosteroids" should read --corticosteroids--.

At column 2, line 62 "relates a" should read --relates to a--.

At column 3, line 3 "Salicyclic" should read --Salicylic--.

At column 3, line 8 "surface" should read --surfactant--.

At column 3, line 43 "instance" should read --instances--.

At column 4, line 39 "emmolient" should read --emollient--.

At column 5, line 19 "%(1986)" should read --(1986)--.

At column 5, line 41 "Multiphases" should read --Multiphase--.

At column 7, line 41 "glyercyl" should read --glyceryl--.

At column 7, line 59 "Quinone" should read --Quinine--.

At column 8, line 21 "chromphore" should read --chromophore--.

At column 9, line 7 "amcinafide." should read --amcinafide,--.

At column 9, line 35 "safapyrn" should read --safapryn--.

At column 9, line 36 "dichlofenac" should read --diclofenac--.

At column 9, line 38 "acetamacin" should read --acematacin--.

At column 9, line 41 "flufenamic niflumic" should read --flufenamic, niflumic--.

At column 9, line 43 "flurbiproflen" should read --flurbiprofen--.

At column 9, line 55 "mefanamic" should read --mefenamic--.

UNITED STATES PATENT AND TRADEMARK OFFICE
CERTIFICATE OF CORRECTION

PATENT NO.    :   5,620,965

DATED         :   April 15, 1997

INVENTOR(S)   :   Roy Lonnie Blank

It is certified that error appears in the above-identified patent and that said Letters Patent is hereby corrected as shown below:

At column 9, line 66 "4-(5'-hexynoyl)-2,6-t-butylphenol" should read --4-(5'-hexynoyl)-2,6-di-t-butylphenol--.

At column 10, line 6 "Issued" should read --issued--.

At column 10, line 56 "furidioxime" should read --furildioxime--.

At column 11, line 13 "0.01" should read --0.01%--.

At column 11, line 39 "-$R^4$;" should be deleted.

At column 11, line 44 "$C_{1\text{-}C18}$" should read --$C_1$-$C_{18}$--.

At column 11, line 47 "is $C_1$-$C_{18}$" should read --is a $C_1$-$C_{18}$--.

At column 12, line 2 "Protestant" should read --protectant--.

At column 12, line 21 "glacturonic" should read --galacturonic--.

At column 12, line 66 "N-cetyl-L-cysteine" should read --N-acetyl-L-cysteine--.

Signed and Sealed this

Fifteenth Day of July, 1997

Attest:

BRUCE LEHMAN

Attesting Officer

Commissioner of Patents and Trademarks